United States Patent
Lowe et al.

(10) Patent No.: US 6,773,599 B1
(45) Date of Patent: Aug. 10, 2004

(54) TRIAZINE-BASED DETOXIFICATION AGENTS AND THEIR USE

(75) Inventors: Christopher Robin Lowe, Cambridge (GB); Kim Hilary Lawden, London (GB)

(73) Assignee: Prometic Biosciences Ltd., British Isles (GB)

( * ) Notice: Subject to any disclaimer, the term of this patent is extended or adjusted under 35 U.S.C. 154(b) by 0 days.

(21) Appl. No.: 10/069,099

(22) PCT Filed: May 9, 2000

(86) PCT No.: PCT/GB00/01759

§ 371 (c)(1),
(2), (4) Date: May 13, 2002

(87) PCT Pub. No.: WO00/67900

PCT Pub. Date: Nov. 16, 2000

(30) Foreign Application Priority Data

May 10, 1999 (GB) .............................................. 9910807

(51) Int. Cl.[7] .............................................. B01D 15/08
(52) U.S. Cl. .................... 210/635; 210/656; 210/198.2; 210/502.1; 530/390.1; 530/413; 530/417
(58) Field of Search ................................ 210/635, 656, 210/659, 198.2, 502.1; 530/390.1, 413, 415, 417

(56) References Cited

U.S. PATENT DOCUMENTS

| | | | | |
|---|---|---|---|---|
| 4,229,537 | A | | 10/1980 | Hodgins et al. ............. 435/177 |
| 4,491,660 | A | | 1/1985 | Gendrich et al. ............. 536/32 |
| 5,202,246 | A | * | 4/1993 | Kruse et al. .................. 435/174 |
| 5,578,455 | A | * | 11/1996 | Tosa et al. .................. 435/7.32 |
| 5,917,022 | A | * | 6/1999 | Davies ..................... 530/390.1 |
| 6,428,703 | B1 | * | 8/2002 | Zinn et al. .................. 210/635 |

FOREIGN PATENT DOCUMENTS

| | | |
|---|---|---|
| EP | 0 350 004 A2 | 1/1990 |
| EP | 0 431 593 A2 | 6/1991 |
| GB | 2 092 470 A | 8/1982 |
| WO | WO 96/41185 | 12/1996 |
| WO | WO 97/10887 | 3/1997 |

OTHER PUBLICATIONS

Burton, Nicolas P. and Christopher R. Lowe "Design of Novel Affinity Adsorbents for the Purification of Trypsin-Like Proteases" *Journal of Molecular recognition* 5:55–68, 1992.

* cited by examiner

Primary Examiner—Ernest G. Therkorn
(74) Attorney, Agent, or Firm—Saliwanchik, Lloyd & Saliwanchik

(57) ABSTRACT

An affinity ligand-matrix conjugate comprises the matrix and, conjugated thereto by the group Z, a ligand having general formula (I) wherein on X is N and the other X is N, CCL or CCn; $A_1$ and $A_2$ are each independently O, S or N—$R_1$ and $R_1$ is H, $C_{1-6}$alkyl, $C_{1-6}$ hydroxyalkyl, benzyl or β-phenylethyl; $B_1$ and $B_2$ are each independently an optionally substituted hydrocarbon lingkage containing from 1 to 10 carbon atoms; $D_1$ is H or a primary amino, secondary amino, tertiary amino, quaternary ammonium, imidazole, guanidino or amidino group; and $D_2$ is a secondary amino, tertiary amino, quaternary ammonium, imadazole, guanidino or amidino group; of $B_2$-$D_2$ is —CHCOOH—$(CH_2)_{3-4}$—$NH_2$; AND p is 0 or 1. Such conjugates are useful for the separation, isolation, purification, characterisation, identification or quantification of an endotoxin.

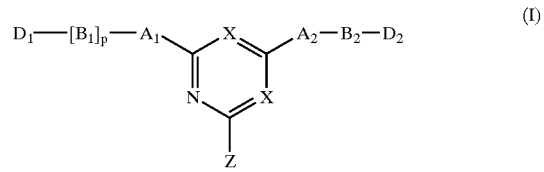

(I)

5 Claims, No Drawings

TRIAZINE-BASED DETOXIFICATION AGENTS AND THEIR USE

Reference to Related Applications

This application is a 371 of PCT/GB00/01759 filed May 9, 2000.

FIELD OF THE INVENTION

The present invention relates to novel affinity ligands, their preparation and attachment to matrices which may consist of solid, semi-solid, particulate or colloidal materials, or soluble polymers. The invention furthermore relates to these novel affinity ligand-matrix conjugates and the preparation and use thereof in the binding and removal of endotoxin from various fluids such as water, aqueous solutions, body fluids, blood, plasma, solutions of pharmaceutical products, proteins and other compounds of biological origin.

BACKGROUND OF THE INVENTION

Endotoxins are lipopolysaccharides found in the outermost membrane of Gram-negative bacteria, particularly pathogeneic bacteria of the class Enterobacteriaceae, Neisseriaceae and Chlamydiaceae. Endotoxins comprise lipid A attached to a polysaccharide of variable structure dependent upon its biological origin. The polysaccharide component of Enterobacteriaceae endotoxin is characterised by an O-specific chain region and a core region. The O-specific region comprises up to 50 repeating oligosaccharide units that contain as many as 8 different sugar residues. O-specific chains exhibit large structural diversity from species to species whereas the core region, divided into the outer core and inner core regions, is less variable. The inner core region is characterised by the presence of unusual sugar residues such as heptose and 2-keto-3deoxyoctonic acid (KDO) which are frequently substituted with phosphate or phosphate derivatives. Also attached to the inner core region, lipid A is a conserved biphosphorylated glucosamine disaccharide which is acylated by 4 saturated primary acyl groups of which 2 carry secondary saturated acyl groups. The combination of hydrophobic lipid A tails with the hydrophilic and anionic polysaccharide unit provides endotoxin with amphipathic properties.

Endotoxin released from the cell wall of Gram-negative bacteria is considered to be the primary cause of the many pathiphysiological occurrences that accompany Gram-negative septicaemia. Endotoxin at pg/ml concentrations in blood triggers the release of a variety of cytokines, including interleukins and TNF. Over stimulation of the immune system by endotoxin leads to a massive release of cytokines which ultimately results in metabolic breakdown and septic shock. During septic shock, the complement and coagulation cascades become activated and vascular permeability increases. This can lead to disseminated intravascular coagulation and multiple organ failure, often with fatal consequences. Septic shock often develops because of the lack of an initial response to infection allowing the level of blood-borne endotoxin to reach critical levels.

In addition to the obvious risk presented by the presence of live Gram negative bacteria or cell wall debris in parenteral pharmaceutical products, the presence of free endotoxin in pharmaceutical preparations is also a major concern. Because endotoxin is such a potent immune stimulator, very low concentrations may cause toxic reactions including pyrogenic effects. Endotoxin is a relatively stable molecule which is not inactivated by routine autoclaving or treatment with organic solvents. Exposure to concentrated sodium hydroxide or prolonged high temperature (250° C.) will inactivate endotoxin, though such methods are not appropriate for most biological products. Furthermore, maintenance of complete sterility throughout the manufacture of bio-therapeutics is problematic. Consequently, the highly efficient capture and removal of endotoxin from parenteral pharmaceuticals is very desirable, particularly in situations where endotoxin is known to associate with components of the therapeutic formulation.

A variety of techniques have been used to remove endotoxin from aqueous solutions including ultrafiltration, charcoal adsorption, cation-exchange chromatography, and a variety of immobilised affinity ligands including polymyxin B and endotoxin binding protein. All of these techniques exhibit significant shortcomings, particularly in the case of endotoxin removal from high molecular weight compounds such as therapeutic proteins. Ultrafiltration can only be used to remove endotoxin from low molecular weight compounds whereas charcoal adsorption tends to promote the binding of most organic compounds. Cation-exchange chromatography is effective in removing endotoxin from water but less effective for protein containing solutions, particularly proteins with acidic isoelectric points. Polymyxin B, a cyclic polypeptide antibiotic, is too toxic to allow its use for the purification of therapeutic products whereas endotoxin binding protein is too expensive for commercial applications.

Immobilised cationic amino acids (histidine, lysine and arginine) have also been used for endotoxin removal (Tosa, T. et al., Molecular Interactions in Bioseparations, Ed. Ngo, T. T., Plenum Press, New York, pp. 323–332, 1993; Lawden, K. H. et al, Bacterial Endotoxins: Lipopolysaccharides From Genes to Therapy, Wiley-Liss Inc., pp. 443–452, 1995). Such materials have been prepared by direct attachment of amino acids to epoxy-activated chromatographic matrices. In the case of Pyrosep™, a commercially available material manufactured by Tanabe Seiyaku. Company Limited, Osaka, Japan, a single histidine group is immobilised to a support matrix by a hexanediamine spacer arm. Again, such materials are adequate for removal of endotoxin from water or solutions of low molecular weight compounds, but their performance is compromised in the presence of salt (>50 mM) or proteins which have an affinity for endotoxin. Consequently, none of the existing methods of endotoxin removal are suited to the elimination of endotoxin from bio-therapeutic compounds intended for parenteral administration. This is especially true for protein therapeutics where no single effective and safe method of endotoxin removal exists.

Removal of endotoxin from blood or plasma may provide an effective approach to the management of septic shock, particularly if applied at the early stages of infection or prophylactically in situations where an increased risk of septic shock is anticipated (e.g. major bowel or liver surgery). Several studies have been reported as to the use of monocolonal antibodies directed against endotoxin or cytokines released in the initial phase of the shock reaction. However, most of these approaches have been found to be ineffective (Siegel, J. P., Drug Information Journal, 30, pp. 567–572, 1996). In contrast, extracorporeal extraction of endotoxin from whole blood has been accomplished by use of fibre-immobilised polymyxin B (Aoki, H. et al., Nippon Geka Gakkai Zasshi (Japan), 94, pp. 775–780, 1993), though concerns over potential toxicity of polymyxin B lechates remain. Consequently, affinity adsorbents incorporating endotoxin binding ligands which have high affinity for endotoxin and low toxicity may also be beneficial for the management of sepsis.

Immobilised amino acids have also been investigated as potential endotoxin removal agents but such materials bind endotoxin weakly and non-specifically and are of limited value in the extraction of endotoxin from biological fluids and solutions of biological compounds. Triazine-based compounds have been reported which bind selectively to proteins; however, such ligands are not applicable to the isolation of endotoxin.

SUMMARY OF THE INVENTION

This invention relates to the discovery of synthetic affinity ligand structures which bind selectively to endotoxin. A generic group of novel affinity ligands have been found which exhibit high affinity for endotoxin and are generally applicable to the isolation of endotoxin from a variety of sources.

A feature of the present invention is the provision of a general tool for the removal of endotoxin contamination from biological materials. Endotoxin binds exceedingly tightly to affinity ligand-matrix conjugates of the invention. This feature enables highly efficient extraction of endotoxin from water and aqueous solutions providing a means of generating pyrogen-free water or pyrogen-free solutions. Affinity ligand-matrix conjugates of the invention are especially valuable for the removal of endotoxin which is bound to or associated with proteins, drugs or other biological compounds intended for medical or pharmaceutical applications. Certain biological compounds, particularly proteins, often bind endotoxin tightly and subsequent removal is very difficult, if not impossible, by existing means. Affinity ligand-matrix conjugates of the invention may also be applied to the removal of endotoxin from blood or plasma and so provide an especially useful tool for in vitro or in vivo removal of endotoxin, the latter being achieved, for example, by way of an extracorporeal endotoxin extraction device. Such a device may be especially valuable for removal of endotoxin which is released into the blood stream during bacterial infections, such infections often causing life-threatening diseases such as septicaemia or meningitis. Removal of blood-borne endotoxin may be particularly beneficial in the treatment of these diseases and in the prevention and management of septic shock.

Novel affinity ligand-matrix conjugates provided by this invention can be used in place of other endotoxin binding materials and are significantly more flexible in their use, are more robust, less expensive to produce and offer greater endotoxin binding efficiencies.

The present invention relates to affinity ligand-matrix conjugates comprising a ligand having General Formula (1):

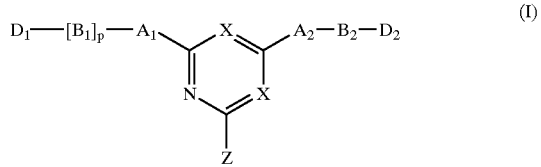

(I)

wherein one of the symbols X represents a nitrogen atom and the other symbol X represents a nitrogen atom or a carbon atom carrying a chlorine atom or a cyano group;

$A_1$ and $A_2$ each independently represent an oxygen atom, a sulphur atom or a group $N-R_1$;

$R_1$ represents a hydrogen atom, an alkyl group containing from 1 to 6 carbon atoms, a hydroxyalkylgroup containing from 1 to 6 carbon atoms, a benzyl group or a β-phenylethyl group;

$B_1$ and $B_2$ each independently represent an optionally substituted hydrocarbon linkage containing from 1 to 10 carbon atoms (any substituent being substantially non-critical with respect to utility) and including alkyl, phenyl, naphthyl and cyclohexyl groups;

$D_1$ represents a hydrogen atom, a primary amino group, a secondary amino group, a tertiary amino group, a quaternary ammonium group, an imidazole group, a guanidino group or an amidino group;

$D_2$ represents a primary amino group (e.g. as derived from lysine or ornithine), a secondary amino group, a tertiary amino group, a quaternary ammonium group, an imidazole group, a guanidino group or an amidino group; and p is 0 or 1.

The ligand is attached to a support matrix in position Z, optionally through a spacer arm interposed between the ligand and matrix. Alternatively, in novel ligands of the invention, Z represents a functional group of the type capable of reaction with a solid matrix that may be activated (if necessary or desired) or unactivated.

DESCRIPTION OF THE INVENTION

When conjugated to a matrix, the optional spacer arm is preferably represented by General Formula (II):

(II)

wherein T represents an oxygen atom, a sulphur atom or a group $N-R_2$; wherein $R_2$ represents a hydrogen atom or an alkyl group containing from 1 to 6 carbon atoms;

V represents an oxygen atom, a sulphur atom, a —COO— group, a CONH group or an NHCO group, a —PO$_3$H group, a NH-arylene-SO$_2$—CH$_2$—CH$_2$— group or a N—R$_3$ group; wherein R$_3$ represents a hydrogen atom or an alkyl group containing from 1 to 6 carbon atoms;

L represents an optionally substituted hydrocarbon linkage containing from 2 to 20 carbon atoms; and m is 0 or 1.

The support matrix may be any compound or material, particulate or non-particulate, soluble or insoluble, porous or non-porous which may be used in conjunction with affinity ligands to form an affinity ligand-matrix conjugate and which provides a convenient means of separating the affinity ligands from solutes in a contacting solution.

The present invention provides novel affinity ligand-matrix conjugates, which affinity ligand-matrix conjugates may be used in the isolation or removal of endotoxin from water, aqueous solutions, body fluids, blood, plasma, solutions of pharmaceutical products, proteins and other compounds of biological origin.

In a preferred embodiment, the invention provides novel affinity ligand-matrix conjugates which are represented by the General Formula (III):

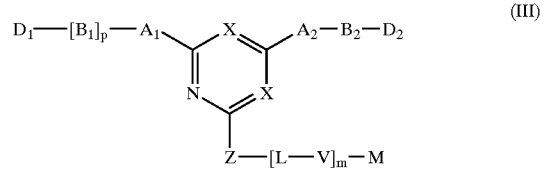

(III)

wherein $A_1$, $A_2$, $B_1$, $B_2$, $D_1$, $D_2$, p, X, T, L, V, m, $R_1$, $R_2$ and $R_3$ have the meanings specified above; and M represents the residue of a support matrix which may be any compound or material, particulate or non-particulate, soluble or insoluble, porous or non-porous which may be used in conjunction with affinity ligands to form an affinity ligand-matrix conjugate and which provides a convenient means of separating the affinity ligands from solutes in a contacting solution.

It will be appreciated that this invention relates, inter alia, to the use of compounds which are pyrimidines, diazines, or triazines carrying a —T—[L—V]$_{0-1}$—M substituent, or the precursor thereof, and other substituents linked to the ring via a hetero atom. Such substituents may include any non-interfering group comprising 0 to 20 carbon atoms.

In the present specification, whenever the term endotoxin is used in a plural or generic sense, it is intended to mean endotoxins originating from any microbiological source. By the term endotoxin is thus also meant lipopolysaccharide from any species including Enterobacteriaceae, Neisseriaceae and Chlamydiaceae. Since endotoxin is known to be heterogeneous, the term "endotoxin" as used herein includes all naturally occurring forms which comprise lipid A covalently linked to a polysaccharide, including analogues, derivatives, fragments and precursors thereof.

The term "primary amino group" as used herein, alone or in combination, refers to an —NH$_2$ group.

The term "secondary amino group" as used herein, alone or in combination, refers to a —NHR$_4$ group; wherein R$_4$ represents a straight or branched alkyl group containing from 1 to 6 carbon atoms.

The term "tertiary amino group" as used herein, alone or in combination, refers to a —NR$_5$, R$_6$ group; wherein R5 and R$_6$ each represent a straight or branched alkyl group containing from 1 to 6 carbon atoms.

The term "quaternary ammonium group" as used herein, alone or in combination, refers to a —NR$_7$, R$_8$, R$_9$$^+$ group; wherein R$_7$, R$_8$ and R$_9$ each represent a straight or branched alkyl group containing from 1 to 6 carbon atoms.

The term "alkyl group containing from 1 to 6 carbon atoms" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butyl, n-pentyl, 2methylbutyl, 3-methylbutyl, n-hexyl, 4-methylpentyl, neopentyl and 2,2-dimethylpropyl.

The term "hydroxyalkyl group containing from 1 to 6 carbon atoms" as used herein, alone or in combination, refers to a straight or branched, saturated hydrocarbon chain having 1 to 6 carbon atoms substituted with one or more hydroxy groups, preferably one hydroxy group, such as e.g. hydroxymethyl, 2-hydroxyethyl, 3-hydroxypropyl, 2-hydroxypropyl, 4-hydroxybutyl, 5-hydroxypentyl and 6hydroxyhexyl.

The term "alkoxy group containing from 1 to 6 carbon atoms" as used herein, alone or in combination, refers to a straight or branched monovalent substituent comprising an alkyl group containing from 1 to 6 carbon atoms linked through an ether oxygen having its free valence bond from the ether oxygen and having 1 to 6 carbon atoms e.g. methoxy, ethoxy, propoxy, isopropoxy, butoxy and pentoxy.

The term "halogen" means fluorine, chlorine, bromine or iodine.

The term "acyloxy or acylamino containing from 1 to 6 carbon atoms" as used herein refers to a monovalent substituent comprising an alkyl group containing from 1 to 5 carbon atoms linked through a carbonyloxy or oxycarbonyl group such as a methylcarbonyloxy, ethylcarbonyloxy, methyloxycarbonyl or ethyloxycarbonyl group or linked through a carbonylamino or aminocarbonyl group such as a methylcarbonylamino, ethylcarbonylamino, methylaminocarbonyl or ethylaminocrbonyl group.

The term "alkysulfonyl containing from 1 to 6 carbon atoms" as used herein refers to a monovalent substituent comprising an alkyl group containing from 1 to 6 carbon atoms linked through a sulfonyl group such as e.g. methylsulfonyl, ethylsulfonyl, n-propylsulfonyl, isopropylsulfonyl, n-butylsulfonyl, sec-butylsulfonyl, isobutylsulfonyl tert-butylsulfonyl, n-pentylsulfonyl, 2-methylbutylsulfonyl, 3-methylbutylsulfonyl, n-hexylsulfonyl, 4-methylpentysulfonyl, neopentylsulfonyl, and 2,2-dimethylpropylsulfonyl.

The term "one or more substituents independently selected from" shall more preferably refer to from 1–3substituents. The term shall further preferably refer to 1–2 substituents and most preferably refer to one substituent.

The term "optionally substituted hydrocarbon linkage containing from 2 to 20 carbon atom" is used herein refers to one or more linear or branched alkyl chains, optionally substituted with for example hydroxy or alkoxy groups containing from 1 to 6 carbon atoms, and optionally linked together by amino, ether, thioether, ester, amide or sulphonamide bonds providing a chain containing from 2 to 20 carbon atoms. The construction is preferably flexible. The construction of such optionally substituted hydrocarbon linkages is for example described in Lowe, C. R. and Dean, P. D. G, 1974, Affinity Chromatography, John Wiley & Sons, London, which is hereby incorporated by reference.

The term "optionally substituted hydrocarbon linkage containing from 1 to 10 carbon atoms" as used herein, alone or in combination, refers to a linear or branched hydrocarbon chain having 1 to 10 carbon atoms optionally substituted with one or more functional groups, including but not limited to, carboxyl groups, preferably one carboxyl group, and hydroxyl groups.

In a preferred embodiment of the invention R$_1$ represents a hydrogen atom.

In another preferred embodiment of the invention, R$_2$ represents a hydrogen atom.

In another preferred embodiment of the invention, R$_3$ represents a hydrogen atom.

In another preferred embodiment of the invention, R$_4$ represents a methyl group, an ethyl group or a propyl group.

In another preferred embodiment of the invention, R$_5$ represents a methyl group, an ethyl group or a propyl group.

In another preferred embodiment of the invention, R$_6$ represents a methyl group, an ethyl group or a propyl group.

In another preferred embodiment of the invention, R$_7$ represents a methyl group, an ethyl group or a propyl group.

In another preferred embodiment of the invention, R$_8$ represents a methyl group, an ethyl group or a propyl group.

In another preferred embodiment of the invention, R$_9$ represents a methyl group, an ethyl group or a propyl group.

In another preferred embodiment of the invention, A$_1$ represents N—R$_1$ wherein R$_1$ is as defined above.

In another preferred embodiment of the invention, A$_2$ represents N—R$_1$ wherein R$_1$ is as defined above.

In another preferred embodiment of the invention, B$_1$ represents a —CHCOOH—CH$_2$— group, a —CHCOOH—(CH$_2$)$_2$— group, a —CHCOOH—(CH$_2$)$_3$— group, a —CHCOOH—(CH$_2$)$_4$— group, an ethyl group, a propyl group, a 2-hydroxypropyl group, a butyl group, a pentyl group, a hexyl group or a phenyl group.

In another preferred embodiment of the invention, B$_2$ represents a —CHCOOH—CH$_2$— group, —CHCOOH—(CH$_2$)$_2$— group a —CHCOOH—(CH$_2$)$_3$— group, a —CHCOOH—(CH$_2$)$_4$— group, ethyl group, a propyl group, a 2-hydroxypropyl group, a butyl group, a pentyl group, a hexyl group or a phenyl group.

In another preferred embodiment of the invention, $D_1$ represents hydrogen, an amino group, an imidazole group, a guanidino group, an aminidino group, a trimethylammonium group, a triethylammonium group, a dimethylamino group, a diethylamino group, a methylamino group or an ethylamino group.

In another preferred embodiment of the invention, $D_2$ represents an amino group, an imidazole group, a guanidino group, an aminidino group, a trimethylammonium group, a triethylammonium group, a dimethylamino group, a diethylamino group, a methylamino group or an ethylamino group. $D_2$ (and often also $D_1$) is preferably a strongly charged species.

In another preferred embodiment of the invention, p represents 0 or 1.

In another preferred embodiment of the invention, both X represent a nitrogen atom.

In another preferred embodiment of the invention, T represents an oxygen atom or, more preferably, an NH group.

In another preferred embodiment of the invention, L represents a butyl, pentyl, hexyl, heptyl, octyl, nonyl, decyl or dodecyl group and V and m are as defined above.

In another preferred embodiment of the invention, V represents an oxygen atom, a —COO— group, a $PO_3H$— group or an $NR_3$ group; and more preferred an oxygen atom or an NH group and L and m are as defined above.

In another preferred embodiment of the invention, m represents 1 and L and V are as defined above.

The term "integer between x and y" may include the values x (including zero) and y.

The invention also provides methods for the manufacture of novel affinity ligand-matrix conjugates according to the invention which comprises reacting, in any order, (i) a halogenoheterocyclic compound of General Formula (IV):

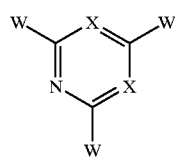

(IV)

wherein the symbols X have the meaning hereinbefore specified and W represents a halogen atom with (ii) a compound of General Formula (V):

(V)

wherein the symbols $D_1$, $B_1$, $A_1$ and p have the meanings hereinbefore specified and H is hydrogen, (iii) a compound of General Formula (VI):

(VI)

wherein the symbols $D_2$, $B_2$ and $A_2$ have the meanings hereinbefore specified and H is hydrogen, and (iv) with either an optionally derivatised support matrix of General Formula (VII):

(VII)

wherein the symbols T, L, V, m and M have the meanings hereinbefore specified and H is hydrogen or, with a linking unit of General Formula (VIII):

(VIII)

wherein the symbols T, L, V have the meanings hereinbefore specified to give a compound of General Formula (IX):

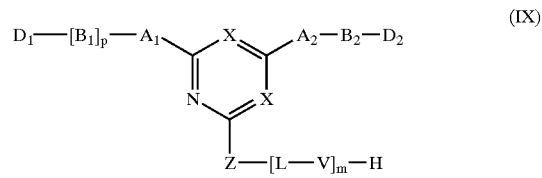

(IX)

wherein $A_1$, $A_2$, $B_1$, $B_2$, $D_1$, $D_2$, p, X, T, L, V, m, $R_1$, $R_2$, $R_3$, $R_4$, $R_5$, $R_6$, $R_7$, $R_8$, and $R_9$ have the meanings hereinbefore specified; the compound of General Formula (IX) is then reacted further with a support matrix whose residue is represented by M using activating and coupling procedures well known to those skilled in the art.

As examples of halogenoheterocyclic compounds of General Formula (IV) there may be mentioned 5-chloro-2,4,6-trifluoropyrimidine, 5-cyano-2,4,6-trichloropyrimidine, cyanuric fluoride, cyanuric bromide and, above all, cyanuric chloride.

As examples o f compounds of General Formula (V) there may be mentioned ammonia, water, arginine, lysine, histidine, α,γ-diaminobutyric acid, m-aminobenzamidine, p-aminobenzamidine, m-aminobenzenetrimethylammonium bromide, p-aminobenzenetrimethylammonium bromide, 2-(diethylamino)ethylamine, (2-aminoethyl) trimethylammonium chloride, histamine, agmatine, ethylenediamine, 1,3-diaminopropane, 1,3-diamino-2-hydroxypropane, 1,4-diaminobutane, 1,5-diaminopentane and 1,6-diaminohexane.

As examples of compounds of General Formula (VI) there may be mentioned arginine, lysine, histidine, α,γ-diaminobutyric acid, m-aminobenzamidine, p-aminobenzamidine, m-aminobenzenetrimethylammonium bromide, p-aminobenzenetrimethylammonium bromide, 2-(diethylamino)ethylamine, (2-aminoethyl) trimethylammonium chloride, histamine, agmatine, ethylenediamine, 1,3-diaminopropane, 1,3-diamino-2-hydroxypropane, 1,4-diaminobutane, 1,5-diaminopentane, 1,6-diaminohexane.

As example of support matrices whose residue is represented by M, there may be mentioned insoluble support matrices such as a naturally occurring polymer, for example a polypeptide or protein such as cross-linked albumin or a polysaccharide such as agarose, alginate, carrageenan, chitin, cellulose, dextran or starch; synthetic polymers such as polyacrylamide, polystyrene, polyacrolein, polyvinyl alcohol, polymethylacrylate or perfluorocarbon; inorganic compounds such as silica, glass, kieselguhr, alumina, iron oxide or other metal oxides or co-polymers consisting of any combination of two or more of a naturally occurring polymer, synthetic polymer or inorganic compounds. Also included within the definition of support matrices whose residue is represented by M are soluble support matrices comprising polymers such as dextran, polyethylene glycol, polyvinyl alcohol or hydrolysed starch, which provide affinity-ligand matrix conjugates for use in liquid partitioning; or support matrices comprising compounds such as perfluorodecalin which provide affinity-ligand matrix conjugates for use in the formation of affinity emulsions. For the avoidance of doubt, a support matrix is defined herein as any compound or material whether particulate or non-particulate, soluble or insoluble, porous or non-porous which may be used to form a novel affinity ligand-matrix conjugate according to the invention and which provides a convenient means of separating the affinity ligand from solutes in a contacting solution.

Also included within the definition of support matrices whose residue is represented by M are support matrices such as agarose, cellulose, dextran, starch, alginate, carrageenan, synthetic polymers, silica, glass and metal oxides which have been, or are, modified by treatment with an activating agent prior to, or during, attachment of the ligand.

In a preferred embodiment of the invention, M represents optionally activated agarose, silica, cellulose, dextran, glass, toyopearl, hydroxyethylmethacrylate, polyacrylamide, styrenedivinylbenzene, Hyper D, perfluorocarbons, polysulphone, polyethersulphone, polyvinylidinefluoride, nylon, and polyvinylchloride. Preferably M represents optionally tresyl-activated, sulphonyl chloride-activated, tosyl-activated, vinylsulphone-activated or epoxy-activated agarose.

There exists a considerable number of activating agents which have found use for the general purpose of attaching ligands to support matrices. These compounds and their method of use are well known to those skilled in the art and, since the nub of the present invention lies in the nature of the ligand attached to the matrix and not in the mode of attachment, any of these activating agents will serve in the preparation of the new matrix-ligand conjugates of the invention. As non-limiting examples of such activating agents there may be mentioned such diverse compounds as cyanogen bromide, cyanuric chlorde, epichlorohydrin, divnyl sulphone, p-toluenesulphonyl chloride, 1,1'-carbonyldiimidazole, sodium meta-periodate, 2-fluro-1-methylpyridiniumtoluene-4-sulphonate, glycidoxypropyltrimethoxysilane and 2,2,2-trifluroethanesulphonyl chloride. As indicated above, the procedures by which such activating steps are carried out are well known to those skilled in the art.

Similarly, a wide variety of condensing agents may be used to attach the compounds of General Formulae (VIII) and (IX) to support matrices such as agarose, cellulose, dextran, starch, alginate, carrageenan, silica or glass. Again these compounds, and their method of use are well known to those skilled in the art and, again, since the nub of the present invention lies in the nature of the ligand and not in the mode of attachment, any of these condensing agents will serve in the preparation of the new matrix-ligand conjugates of the invention. As non-limiting examples of such condensing agents, there may be mentioned N-ethoxycarbonyl-2-ethoxy-1,2-dihydroquinoline, dicyclohexyl carbodiimide and 1-ethyl-3-(3-dimethylaminopropyl)carbodiimide.

As examples of linking units of General Formula (VIII) which may be used to produce compounds of General Formula (IX) there may be mentioned diamines such as ethylenediamine, N,N'-dimethylethylenediamine, N-ethylethylenediamine, N-(β-hydroxyethyl) ethylenediamine, propylenediamine, N-methylpropylenediamine, N-(β-hydroxyethyl)propylenediamine, 1,4-diaminobutane, 1,5-diaminopentane, 1,6-diaminohexane, 1,7-diaminoheptane, 1,8-diaminooctane, 1,9-diaminononane, 1,10-diaminodecane, 1,12-diamindodecane, piperazine, 3hydroxy-1,5-diaminopentane, m- and p-phenylene diamine, m- and p aminobenzylamine; amino alcohols such as ethanolamine, N-methylethanolamine, N-propylethanolamine, diethanolamine, 3-hydroxypropylamine, 2,3-dihydroxypropylamine, isopropanolamine, 5-aminopentan-1-ol and 6-aminohexan-1-ol; aminophenols such as o-, m- and p-aminophenol, aminocarboxylic acids such as glycine, N-methylglycine, 3- and 4-aminobutyric acid, 3-aminoisobutyric acid, 5-aminovaleric acid, 6-aminocaproic acid; 7-aminoheptanoic acid, m- and p-aminobenzoic acid; aminophosphonic acids such as m-aminobenzenephosphonic acid and p-aminobenzylphosphonic acid; and aminoarylene vinylsulphone precursors such as aniline-3-β-sulphatoethylsulphone and aniline-4-β-sulphatoethylsulphone.

The reaction of halogenoheterocyclic compounds of General Formula (IV) with compounds of General Formulae (V), (VI) and (VII) or (VIII) may be carried out in an organic solvent which is not miscible with water; or in an organic solvent which is miscible with water, or in a mixture of water and a water miscible organic solvent. Examples of suitable organic solvents which are not miscible with water are toluene, xylene or chlorobenzene; examples of suitable organic solvents which are miscible with water are acetone, methyl ethyl ketone or dioxan. The first reaction of the halogenoheterocyclic compound may be carried out at temperatures between 0° C. and 25° C., ideally between 0° C. and 5° C.; the second reaction may be carried out at temperatures between 20° C. and 50° C., ideally between 30° C. and 45° C. and the third reaction at temperatures between 20° C. and 100° C. During such reactions, the inorganic acid such as hydrochloric acid or hydrofluoric acid which is produced is neutralised by the use of an acid binding agent such as sodium hydroxide, sodium carbonate, sodium bicarbonate, calcium hydroxide or calcium carbonate.

Additionally, compounds of General Formula (IX) may be reacted with a reactive polymerisable monomer to form a polymerisable compound of General Formula (X):

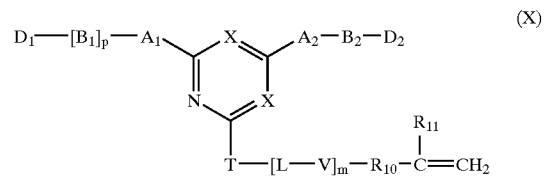

wherein $A_1$, $A_2$, $B_1$, $B_2$, $D_1$, $D_2$, p, X, T, L, V, m, $R_1$, $R_2$, $R_3$, $R_4$, $R_5$, $R_6$, $R_7$, $R_8$, and $R_9$ have the meanings hereinbefore specified; $R_{11}$ represents a hydrogen atom or an alkyl group containing from 1 to 6 carbon atoms; $R_{10}$ represents a carbonyl group, a methylene group, a —NH—CH—$CH_2$— group or a —S—$CH_2$— group. Examples of reactive polymerisable monomers include acryloyl chloride, methacryloyl chloride, allyl bromide, allylamine or 3,4-epoxybutene. Polymerisable compounds of General Formula (X) may be polymerized, optionally in the presence of other polymerisable monomers, to form affinity ligand matrix conjugates of General Formula (III). Such polymerisation procedures are well known to those skilled in the art.

In another embodiment the invention relates to novel affinity ligand matrix conjugates of General Formula (XI):

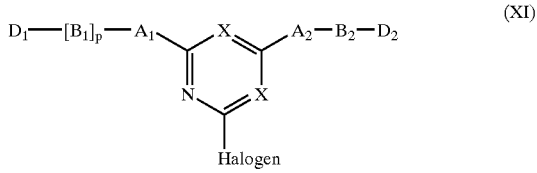

wherein $A_1$, $A_2$, $B_1$, $B_2$, $D_1$, $D_2$, p, X, $R_1$, $R_2$, $R_3$, $R_4$, $R_5$, $R_6$, $R_7$, $R_8$, and $R_9$, have the meanings hereinbefore specified and Halogen represents a fluorine, chlorine, bromine or iodine atom.

Furthermore, the invention relates to a method of attaching novel affinity ligands of General Formula (XI) as defined above to a matrix of General Formula (VII) as defined above by reacting the novel affinity ligands with the matrix at temperatures between 0° C. and 100° C., optionally in the presence of an acid binding agent.

In another embodiment the invention relates to novel affinity ligands of General Formula (XII):

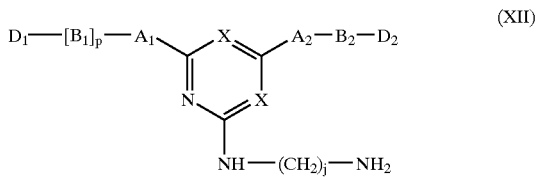

wherein $A_1$, $A_2$, $B_1$, $B_2$, $D_1$, $D_2$, p, X, $R_1$, $R_2$, $R_3$, $R_4$, $R_5$, $R_6$, $R_7$, $R_8$ and $R_9$ have the meanings hereinbefore specified and j is an integer between 2 and 20.

Furthermore, the invention relates to a method of preparing above novel affinity ligands by reacting a compound of above General Formula (XI) with an alkylene diamine of General Formula $H_2-(CH_2)_j-NH_2$ at temperatures between 0° C. and 100° C., optionally in the presence of an acid binding agent.

In another embodiment the invention relates to novel affinity ligands of General Formula (XIII):

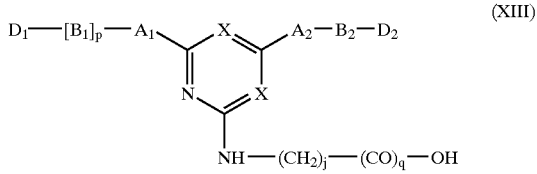

wherein $A_1$, $A_2$, $B_1$, $B_2$, $D_1$, $D_2$, p, X, $R_1$, $R_2$, $R_3$, $R_4$, $R_5$, $R_6$, $R_7$, $R_8$, and $R_9$ have the meanings hereinbefore specified; j is an integer between 2 and 20, and q is 0 or Furthermore, the invention relates to a method of attaching novel affinity ligands of General Formula (XIII) as defined above to a matrix of General Formula (VII) as defined above by reacting the novel affinity ligands with the matrix at temperatures between 0° C. and 100° C. in the presence of a condensing agent. As non-limiting examples of such condensing agents, there may be mentioned N-ethoxycarbonyl-2-ethoxy-1,2-dihydroquinoline, dicyclohexyl carbodiimide and 1-ethyl-3-(3-dimethylaminopropyl)-carbodiimide.

Furthermore, the invention relates to a method of preparing novel affinity ligands of above General Formula (XIII) by reacting a compound of above General Formula $H_2N-(CH_2)_j-(CO)_q-OH$ at temperatures between 0° C. and 100° C., optionally in the presence of an acid binding agent.

In another embodiment, the invention relates to novel affinity ligands of above General Formula (X) wherein $A_1$, $A_2$, $B_1$, $B_2$, $D_1$, $D_2$, p, X, T, L, V, m, $R_1$, $R_2$, $R_3$, $R_4$, $R_5$, $R_6$, $R_7$, $R_8$, and $R_9$ have the meanings hereinbefore specified; $R_{10}$ represents a hydrogen atom or an alkyl group containing from 1 to 6 carbon atoms; $R_{11}$ represents a carbonyl group, a methylene group, a $-NH-CH_2-$ group or a $-S-CH_2-$ group; preferably L is an alkyl group containing from 4 to 10 carbon atoms, preferably T represents a $-NH-$ group, preferably V represents a $-NH-$ group and m is preferably 1.

In a preferred embodiment the invention relates to novel affinity ligands of General Formula (XIV):

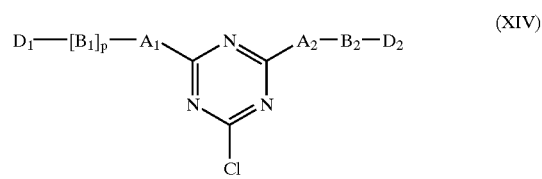

wherein $A_1$, $A_2$, $B_1$, $B_2$, $D_1$, $D_2$, p and $R_1$ have the meanings specified above.

In another preferred embodiment, the invention relates to novel affinity ligands of General Formula (XV):

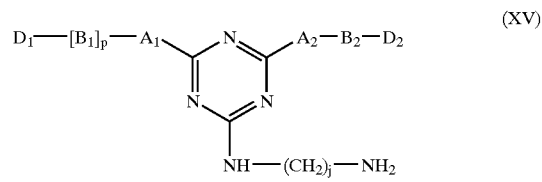

wherein $A_1$, $A_2$, $B_1$, $B_2$, $D_1$, $D_2$, p and $R_1$ have the meanings specified above and j is an integer between 2 and 20.

In another preferred embodiment, the invention relates to affinity ligands of General Formula (X), (XI), (XII), (XIII), (XIV) and (XV) wherein D1 and D2 both independently represent a guanidino group, an imidazole group, a primary amino group, a diethylamino group, a trimethylammonium group or a triethylammonium group.

In another preferred embodiment, the invention relates to affinity ligands of General Formula (IX), (X), (XI), (XII), (XIII), (XIV) and (XV) wherein p is 1.

In another preferred embodiment, the invention relates to affinity ligands of General Formula (IX), (X), (XI), (XII), (XIII), (XIV) and (XV) wherein B1 and B2 both independently represent a $-CHCOOH-(CH_2)_3-$ group, a $-CHCOOH-(CH_2)_4-$ group, a butyl group, a pentyl group or a phenyl group.

In another preferred embodiment, the invention relates to affinity ligands of General Formula (IX), (X), (XI), (XII), (XIII), (XIV) and (XV) wherein A1 and A2 both independently represent a $-NH-$ group.

In another preferred embodiment, the invention relates to affinity ligands of General Formula (IX), (X), (XI), (XII) and (XIII) wherein X represents a nitrogen atom.

In another preferred embodiment, the invention relates to affinity ligands of General Formula (XII), (XIII) and (XV) wherein j is between 4 and 10.

Preferred affinity ligands according to the invention are:

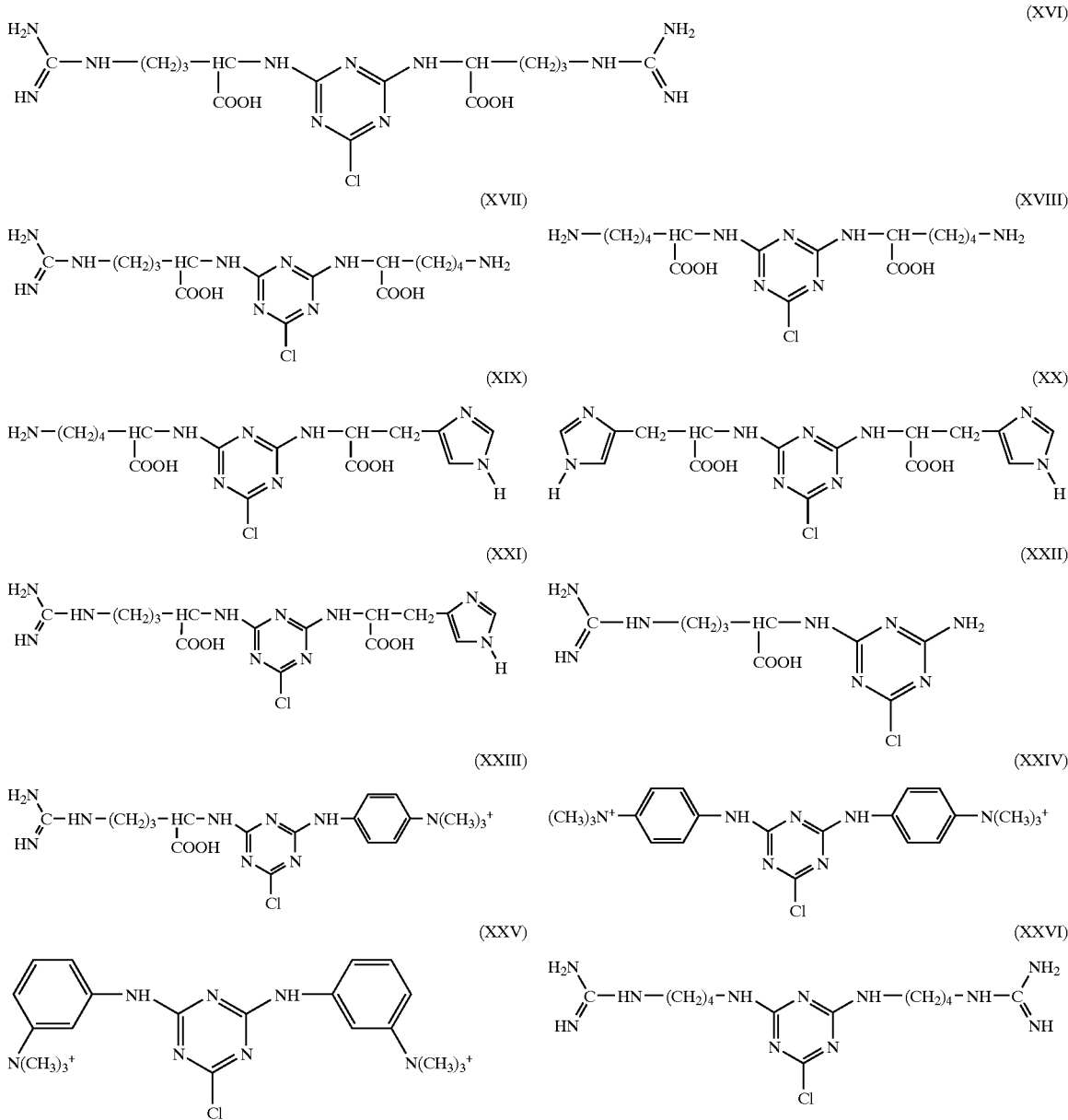

A valuable group of affinity ligand-matrix conjugates is represented by the General Formula (XXVII):

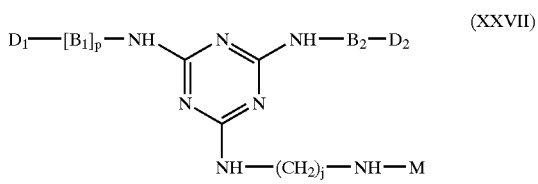

wherein $B_1$, $B_2$, $D_1$, $D_2$, p, M, $R_1$, $R_2$ and $R_3$ have the meanings hereinbefore specified and j is an integer between 4 and 10.

An especially valuable group of affinity ligand support matrices is represented by the General Formula (XXVIII):

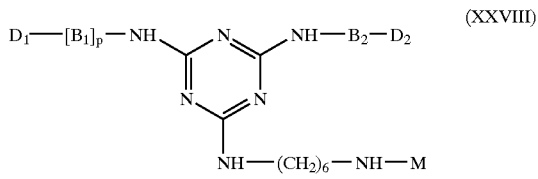

wherein $B_1$, $B_2$, $D_1$, $D_2$, p, X, M, $R_1$, $R_2$, $R_3$ and M have the meanings hereinbefore specified.

Typically, reaction of compounds of General Formula (XXIX):

with 3-propoxy-(1,2-epoxy) derivatised matrices at temperatures between 10° C. and 30° C. in the presence of an acid binding agent produces novel affinity-ligand matrix conjugates which are of outstanding value in the binding of endotoxin from water, aqueous solutions, proteins, drugs, blood and plasma.

Preferred affinity ligand matrix conjugates according to the invention are

-continued

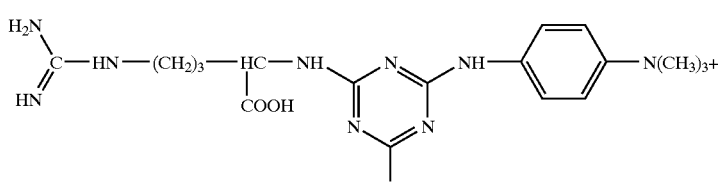

(XXXVII)

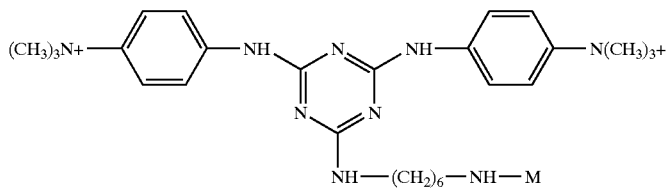

(XXXVIII)

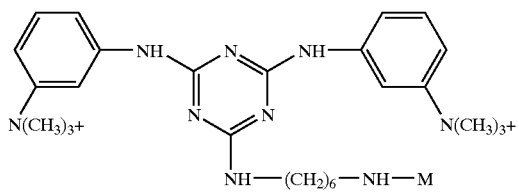

(XXXIX)

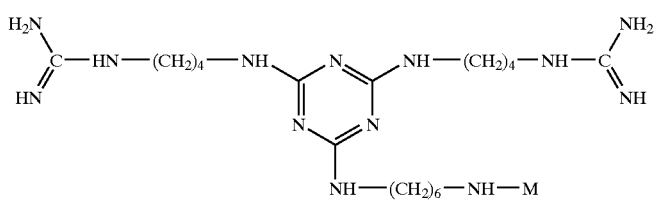

(XXXX)

wherein M is as defined above.

The invention further covers the use of all such affinity ligand-support matrices in the separation, isolation, purification, quantification, identification and characterisation of endotoxin or analogues, fragments, derivatives thereof and precursors.

Endotoxins are a family of lipopolysaccharides, often abbreviated as LPS, which share a common structure. Endotoxins exist in a number of forms, for example the most significant endotoxin types comprising lipid A attached to a core polysaccharide component which may also be linked to a O-specific chain polysaccharide. The core polysaccharide component may consist of an inner core, an inner core attached to an outer oligosaccharide or an inner core attached to an outer core. Endotoxin is known to be extremely heterogeneous, particularly with respect to the O-Specific Chain polysaccharide and the outer core polysaccharide. Since endotoxin is known to be heterogeneous, the term "endotoxin" as used herein includes all naturally occurring forms which comprise lipid A covalently linked to a polysaccharide, including analogues, derivatives, fragments and precursors thereof and all such forms, irrespective of their source, are subject to the claims of this invention.

Furthermore, the invention relates to a method of attaching the novel affinity ligands of General Formulae (IX) as defined above, (X) as defined above, (XII) as defined above, (XV) as defined above and (XXIX) as defined above to carbohydrate or organic polymer matrices by reacting the carbohydrate or organic polymer matrix with an activating agent followed by reaction of the activated matrix with the novel affinity ligand, optionally in the presence of an acid binding agent. The invention also relates to a method of attaching the novel affinity ligands of General Formulae (XIII) as defined above to carbohydrate or organic polymer matrices by condensation with the matrix. The invention furthermore relates to a method of attaching the novel affinity ligands of General Formulae (IX) as defined above, (X) as defined above, (XII) as defined above, (XV) as defined above and (XXIX) as defined above to metal oxide, glass or silica matrices, optionally coated with an organic polymer by reacting the optionally coated metal oxide, glass or silica matrix with an activating agent followed by reaction of the activated matrix with the novel affinity ligand, optionally in the presence of an acid binding agent. Another embodiment of the invention relates to a method of attaching the novel affinity ligands of General Formulae (XIII) as defined above to metal oxide, glass or silica matrices optionally coated with an organic polymer by condensation with the matrix. In another embodiment the invention relates to a method of attaching novel affinity ligands of General Formula (XI) as defined above, (XIV) as defined above and (XVI–XXVI) as defined above to a matrix of General Formula (VII) as defined above by reacting the novel affinity ligands with the matrix at temperatures between –0° C. and 100° C., optionally in the presence of an acid-binding agent. The invention also relates to all the affinity ligand-matrix conjugates, prepared as described in the above methods.

In another embodiment, the invention relates to the use of the affinity ligands according to the invention and the affinity ligand-matrix conjugates according to the invention for the separation, isolation, purification, characterisation, identification or quantification of endotoxin. In another embodiment the invention relates to any process whereby endotoxin containing solutions or liquids are applied to affinity ligand-matrix conjugates according to the invention at a pH in the range 1.0 to 13.0. The invention also relates to a process for the isolation of endotoxin from various fluids such as water, aqueous solutions, body fluids, blood, plasma, solutions of pharmaceutical products, proteins and other compounds of biological origin by carrying out affinity chromatography using as the biospecific ligand a ligand of General Formula (I) as defined above.

Another embodiment of the invention relates to the use of affinity ligands according to the invention and affinity ligand-matrix conjugates comprising such ligands according to the invention for the extracorporeal removal of endotoxin from whole blood or plasma which is taken from a donor and re-infused back into the same donor or another recipient following treatment.

The invention will now be described in further detail with reference to the following Examples. The examples are provided for illustrative purposes and are not to be construed as limiting the scope of the invention in any way.

Example 1

This Example illustrates the synthesis of a typical affinity ligand of General Formula (XIV) defined by the reaction of a halogenohetercyclic compound of General Formula (IV) with a compound of General Formula (V) and (VI).

A solution of 1 part cyanuric chloride in 10 parts acetone was added dropwise to a stirred solution comprising 2 parts L-arginine in 100 parts water. The mixture was stirred for 2 hours at 0–5° C. whereupon the solution was warmed to 30° C. and mixing continued for a further 16 hours. The pH was maintained within the range 5.0–7.0 throughout by titration with 1M sodium hydroxide solution. The reaction product was precipitated by the addition of solid sodium chloride to a final concentration of 20% (w/v), filtered and dried in-vacuo. TLC analysis (THF/propan-2-ol/water (1:2:1 by vol.) solvent) revealed the presence of a single reaction product ($R_f$ 0.42). The molecular mass of the isolated compound was determined by mass spectroscopy and found to be consistent with a compound comprising cyanuric chloride derivatised with 2 molecules of arginine (calculated $M_r$=459.5; molecular ion (+ve FAB)=460.3, (–ve FAB) =458.4). The $^1$H—NMR spectrum was consistent with a compound containing arginine.

Example 2

This Example illustrates the synthesis of an optionally derivatised support matrix of General Formula (VII).

A solution of 1 part 1,6-diaminohexane in 12 parts water was added to a stirred suspension comprising 29 parts epoxy-activated agarose beads (30 μmol epoxide groups per g agarose gel) in 48 parts water and stirred for 24 h at 30° C. The amino-hexyl agarose gel was filtered and washed consecutively with 12×29 parts water and allowed to drain under gravity on completion of the final wash. Analysis of the resulting amino-hexyl agarose for the presence of primary amines (TNBS asay) and epoxide groups (thiosulphate/sodium hydroxide titration) revealed complete reaction of the epoxide groups with 1,6-diaminohexane.

Example 3

Example 2 was repeated by replacing 1,6-diaminohexane with 1,4-diaminobutane, 1,5-diaminopentane, 1,7-diaminoheptane, 1,8diaminooctane, 1,9-diaminononane and 1,10-diaminodecane. In all cases amino-alkyl derivatised agarose matrices were obtained.

Example 4

This Example illustrates the reaction of an optionally derivatised support matrix of General Formula (VII) with a halogenoheterocyclic compound of general formula (IV).

A solution of 1 part cyanuric chloride in 10 parts acetone was added to a pre-cooled (0–4° C.) suspension of 40 parts amino-hexyl agarose matrix prepared according to Example 2 in 40 parts of 0.5M potassium phosphate buffer, pH 7.0. The mixture was stirred for 1 hour at 0–4° C., filtered and washed consecutively with 5×40parts of a solution comprising 1 part acetone and 1 pad water, 5×40 parts water, 5×40 parts of a solution comprising 1 part acetone and 1 part water and 10×40 parts water. Analysis of the resulting dichlorotriazine-activated agarose matrix for the presence of amines (TNBS assay) and release of chloride ions following treatment with 1M sodium hydroxide revealed complete reaction of cyanuric chloride with the primary amino groups on the aminohexyl agarose matrix.

Example 5

Example 4was repeated by replacing the product prepared according to Example 2 with the products prepared according to Example 3. Analysis of the resulting dichlorotriazine-activated agarose matrices for the presence of amines (TNBS assay) and release of chloride ions following treatment with 1M sodium hydroxide revealed in all cases the complete reaction of cyanuric chloride with the primary amino groups on the aminoalkyl agarose matrix.

Example 6

This Example illustrates the reaction of the product prepared according to Example 4 with a compound of General Formula (VI) and a compound of General Formula (V) to produce affinity ligand-matrix conjugates of General Formula (III). All solutions were prepared with pyrogen free water.

One part arginine was added to a suspension containing 35 parts of the product prepared according to Example 4 in 105 parts of 0.1M sodium carbonate buffer, pH 10.25. The mixture was stirred for 24 hours at 30° C., filtered and washed consecutively with 12×35 parts of 0.1M sodium carbonate buffer, pH 10.25 and allowed to drain under gravity. This material was re-slurried in 105 parts of 0.1M sodium carbonate buffer, pH 10.25.

One part N-ε-t-BOC-L-lysine was added to the agarose slurry and the mixture agitated for 72 hours at 85° C. The suspension was filtered and washed consecutively with 12×35 parts of water and allowed to drain under gravity. The mixture was resuspended in 35 parts 0.1M trifluoroacetic acid, stirred for 1 hour at 20° C., filtered and washed consecutively with 3×35 parts methanol, 12×35 parts of water and allowed to drain under gravity. This procedure is required to remove the t-BOC protecting group.

Examples 7 to 14

Table 1 gives further examples of the synthesis of novel affinity ligand-matrix conjugates of the invention which were prepared by the above method but with arginine replaced by the amine compound listed in Column II of Table 1, and N-ε-t-BOC-L-lysine replaced by the amine compound listed in Column III of Table 1. The number of the Example is given in Column I of Table 1.

TABLE 1

| I | II | III |
|---|----|-----|
| 7 | Arginine | Arginine |
| 8 | Arginine | Ammonia |

TABLE 1-continued

| I  | II                    | III                   |
|----|-----------------------|-----------------------|
| 9  | N-im-Trityl-L-histidine | Arginine            |
| 10 | N-ϵ-t-BOC-L-lysine    | N-im-Trityl-L-histidine |
| 11 | N-ϵ-t-BOC-L-lysine    | N-ϵ-t-BOC-L-lysine    |
| 12 | N-im-Trityl-L-histidine | N-im-Trityl-L-histidine |
| 13 | N-im-Trityl-L-histidine | Ammonia             |
| 14 | N-ϵ-t-BOC-L-lysine    | Ammonia               |

Example 15

This example illustrates the ability of affinity ligand-matrix conjugates of General formula (III) to bind endotoxin from water.

Affinity ligand-matrix conjugate (150 µl) prepared according to Example to water (1.5 ml) containing *Escherichia coli* #055:B5 endotoxin ($1.5 \times 10^4$ EU) and agitated for 1 hour at 20° C. The sample was centrifuged and the supernatant assayed for the presence of endotoxin by the Limulus Amoebocyte Lysate Chromogenic Test. Only 0.1 EU/ml (equivalent to 10 pg/ml) was detected in the supernatant indicating greater than 99.99% removal of endotoxin from water.

Examples 16 to 23

Table 2 gives further examples of the ability of novel affinity ligand-matrix conjugates of the invention to bind endotoxin. The procedure described above was performed except that the affinity ligand-matrix conjugate was synthesised according to the Example number given in Column II of Table 2, the amount of endotoxin remaining in the supernatant (EU/ml) is given in Column III of Table 2 and the amount of endotoxin adsorbed (%) by the affinity ligand-matrix conjugate is given in Column IV of Table 2. The number of the Example is given in Column I of Table 2.

TABLE 2

| I  | II | III | IV     |
|----|----|-----|--------|
| 16 | 7  | 1.2 | 99.99  |
| 17 | 8  | 1.1 | 99.99  |
| 18 | 9  | 1.1 | 99.99  |
| 19 | 10 | 7.3 | 99.93  |
| 20 | 11 | 0.4 | >99.99 |
| 21 | 12 | 0.1 | >99.99 |
| 22 | 13 | 1.4 | 99.99  |
| 23 | 14 | 1.0 | 99.99  |

Example 24

This Example illustrates the ability of affinity ligand-matrix conjugates of General Formula (III) to isolate endotoxin from protein containing solutions contaminated with endotoxin.

Affinity ligand-matrix conjugate (150 µl) prepared according to Example 6 was added to water (1.5 ml) containing *Escherichia coli* #:055: B5 endotoxin ($1.5-10^4$ EU) and human serum albumin (15 mg) and agitated for 1 hour at 20° C. The sample was centrifuged and the supernatant assayed for the presence of endotoxin by the Limulus Amoebocyte Lysate Chromogenic Test which had been calibrated to detect endotoxin in the presence of 10 mg/ml human serum albumin. Endotoxin at a concentration of 50 EU/ml was detected in the supernatant indicating 99.5% removal of endotoxin from a solution containing 10 mg/ml human serum albumin.

Examples 25 to 32

Table 3 gives further examples of the ability of novel affinity ligand-matrix conjugates of the invention to isolate endotoxin from protein containing solutions contaminated with endotoxin. The procedure described above was performed except that the affinity ligand-matrix conjugate was synthesised according to the Example number given in Column II of Table 3, the amount of endotoxin remaining in the supernatant (EU/ml) is given in Column III of Table 3 and the amount of endotoxin adsorbed (%) by the affinity ligand-matrix conjugate is given in Column IV of Table 3. The number of the Example is given in Column I of Table 3.

TABLE 3

| I  | II | III | IV   |
|----|----|-----|------|
| 25 | 7  | 790 | 92.1 |
| 26 | 8  | 169 | 98.3 |
| 27 | 9  | 127 | 98.7 |
| 28 | 10 | 81  | 99.2 |
| 29 | 11 | 90  | 99.1 |
| 30 | 12 | 277 | 97.2 |
| 31 | 13 | 54  | 99.5 |
| 32 | 14 | 66  | 99.3 |

Example 33

This Example illustrates the capacity of novel affinity ligand-matrix conjugates of General Formula (III) to bind endotoxin in the presence of protein. Affinity ligand-matrix conjugate (150 µl) prepared according to Example 6 was added to water (1.5 ml) containing *Escherichia coli* #055:B5 endotoxin ($7.5 \times 10^3$ EU to $1.5 \times 10^5$ EU) and human serum albumin (15 mg) and agitated for 1 hour at 20° C. The samples were centrifuged and the supernatants assayed for the presence of endotoxin by the Limulus Amoebocyte Lysate Chromogenic Test which had been calibrated to detect endotoxin in the presence of 10 mg/ml human serum albumin. The total amount of endotoxin present in the uptake mixture and the amount of endotoxin adsorbed is given in Table 4.

TABLE 4

| Total Endotoxin (EU) | Endotoxin Bound (%) |
|----------------------|---------------------|
| $7.5 \times 10^3$    | >99.9               |
| $1.5 \times 10^4$    | 99.5                |
| $3 \times 10^4$      | 99.7                |
| $4.5 \times 10^4$    | 99.6                |
| $7.5 \times 10^4$    | 99.6                |
| $1.5 \times 10^5$    | 99.3                |

These results demonstrate 1 g of novel affinity ligand-matrix conjugate of General Formula (III) is able to bind $1 \times 10^6$ EU (100 µg endotoxin) in the presence of 10 mg/ml human serum albumin with an extraction efficiency of greater than 99%.

Example 34

This Example illustrates the ability of novel affinity ligand-matrix conjugates of General Formula (III) to bind endotoxin in the presence of protein and buffer of varying ionic strength. Affinity ligand-matrix conjugate (150 µl) prepared according to Example 6 was added to water (1.5 ml) containing *Escherichia coil* #055:B5 endotoxin ($7.5 \times 10^4$ EU), human serum albumin (15 mg) and PBS buffer (0 to 200 mM) and agitated for 1 hour at 20° C. The samples were centrifuged and the supernatants assayed for the presence of endotoxin by the Limulus Amoebocyte Lysate Chromogenic Test which had been calibrated to detect endotoxin in the presence of 10 mg/ml human serum albumin. More than 99% of the endotoxin present was adsorbed for all concentrations of PBS buffer investigated. These results demonstrate that novel affinity ligand-matrix conjugates of General Formula (III) are able to bind endotoxin with high efficiency and independently of ionic strength or the presence of protein.

What is claimed is:

1. A method for the removal, separation, isolation, purification, characterization, identification or quantification of an endotoxin; wherein said method removing, separating, purifying, characterizing, identifying, or quantifying an endotoxin with an affinity ligand or conjugate having the general formula (I):

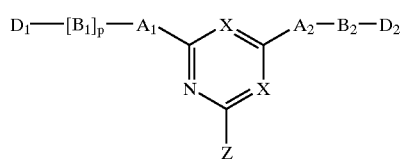

(I)

wherein one X is N and the other X is N, CCl or CCN;

Z is a functional group capable of reaction with a solid matrix;

$A_1$ and $A_2$ are each independently O, S or N—$R_1$ and $R_1$ is H, $C_{1-6}$ alkyl, $C_{1-6}$ hydroxyalkyl, benzyl or β-phenylethyl;

$B_1$ and $B_2$ are each independently an optionally substituted hydrocarbon linkage containing from 1 to 10 carbon atoms;

$D_1$ is H or a primary amino, secondary amino, tertiary amino, quaternary ammonium, imidazole, guanidine or amidino group; and $D_2$ is a secondary amino, tertiary amino, quaternary ammonium, imidazole, guanidine or amidino group; or $B_2$-$D_2$ is —CHCOOH—$(CH_2)_{3-4}$—$NH_2$; and p is 0 or 1.

2. The method according to claim 1, removing an endotoxin from water or an aqueous solution, body fluid, blood, plasma, solution of pharmaceutical products, protein or other compound of biological origin.

3. The method according to claim 2, which comprises extracorporeally removing endotoxin with the conjugate from whole blood or plasma, prior to re-infusion into the donor or another recipient.

4. The method according to claim 1, wherein the endotoxin originates from a Gram-negative bacterium.

5. The method according to claim 1, in an endotoxin-containing solution or liquid is applied to the conjugate at a pH of 1.0 to 13.0.

* * * * *